United States Patent [19]

Sutherland et al.

[11] Patent Number: 4,730,615

[45] Date of Patent: Mar. 15, 1988

[54] STERNUM CLOSURE DEVICE

[75] Inventors: Lloyd A. Sutherland, Levittown, N.Y.; Alfred V. Vasconcellos, Edison, N.J.

[73] Assignee: Pfizer Hospital Products Group, Inc., New York, N.Y.

[21] Appl. No.: 835,394

[22] Filed: Mar. 3, 1986

[51] Int. Cl.$^4$ .................... A61B 17/08; B65D 63/00; B65D 77/10

[52] U.S. Cl. .................... 128/335; 128/339; 24/30.5 P; 24/16 PB

[58] Field of Search .................... 128/339, 335, 346; 24/16 PB, 16 R, 30.5 P, 30.5 R, 20 R

[56] References Cited

U.S. PATENT DOCUMENTS

| | | | |
|---|---|---|---|
| 3,570,497 | 3/1971 | Lemole | 128/339 |
| 3,577,601 | 5/1971 | Mariani et al. | 128/335 |
| 3,802,438 | 4/1974 | Wolvek | 128/335 |
| 3,926,193 | 12/1975 | Hasson | 128/335 |
| 4,201,215 | 5/1980 | Crossett | 128/335 |
| 4,279,248 | 7/1981 | Gabbay | 128/92 |
| 4,535,764 | 8/1985 | Ebert | 128/335 |

*Primary Examiner*—Richard C. Pinkham
*Assistant Examiner*—Gary Jackson
*Attorney, Agent, or Firm*—Peter C. Richardson; Lawrence C. Akers; John L. LaPierre

[57] ABSTRACT

A sternum closure device for closing the sternum of a patient comprising a head portion, tail portion and flexible spine portion. The head portion includes a locking tang to prevent backward movement of the spine portion once it is received and engaged in the head portion. The spine is made of a biocompatible metal coated with a biocompatible polymer along part of its length. One end of the spine is sharpened to serve as a needle. The tang pierces the polymer and locks against a serration of the spine. A method of using the sternum closure device is also disclosed.

9 Claims, 6 Drawing Figures

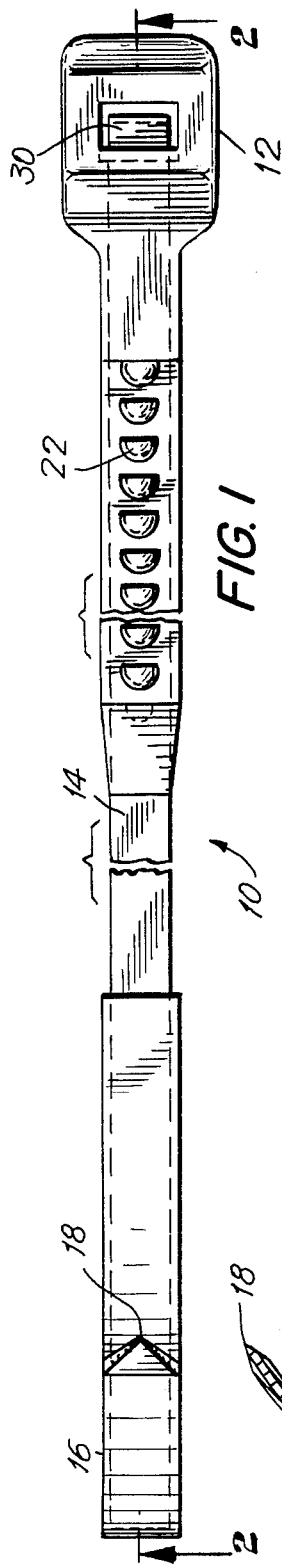
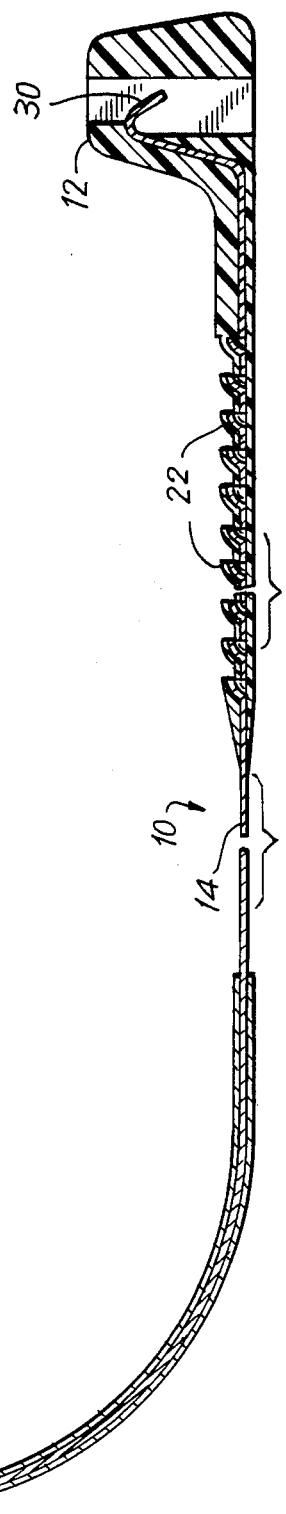
FIG. 1
FIG. 2

STERNUM CLOSURE DEVICE

BACKGROUND OF THE INVENTION

The present invention relates to a sternum closure device and the method of use for closing a split sternum on the body of a patient. More particularly, it relates to a device which has a locking means to prevent backward movement of the sternum once the closure device is engaged.

Current methods used to close a sternum that has been split, typically during open heart surgery, include use of steel sutures or Dacron sutures placed either around or through the sternum. The major difficulty in using Dacron sutures in this procedure is the inadequate material strength of the suture and the inability to obtain the required tension using the dacron sutures which is necessary to close the sternum.

The major difficulty with using steel sutures is that the amount of force necessary to close the sternum may cause the wire to pull through the sternum, cutting the bone in its path, which is known as sternal dehiscense. Steel sutures also have difficulties in closure failure, i.e. overtwisting the suture results in hardening of the suture and breakage. A further disadvantage is that the use of wire sutures, which after being twisted together must be cut off, leaving sharp ends which are both palpable through the skin and cosmetically undesirable. Additionally, the force that a steel suture can apply is limited. Therefore the approximation of the sternum halves joined by this method is not as complete as desired. Sternum bone heals more quickly and with fewer complications when the bone is tightly joined.

SUMMARY OF THE INVENTION

The device of the present invention overcomes the technical, surgical and practical shortcomings of the prior art. An important feature of the present invention is the locking mechanism which engages the spine portion, preventing it from backward movement once the spine portion is fully engaged. A further important feature is that the needle end is integral with the spine portion and is sharp enough to pierce intercostal tissue.

The device of the present invention combines all these features in one closure device. These features, and other features discussed hereinafter, result in a closure device which is more efficient and also promotes better healing in the body of a patient. Further, the closure device of the present invention provides less time and effort in surgery, and prevention of the problem of wire suture pull-through.

The present invention relates to a sternum closure device comprising a head portion, a flexible spine portion, and a tail portion. The head portion is adapted to receive the tail portion and the spine portion. The head portion has a locking means to engage the spine portion such that when the spine portion is received in the head portion it is prevented from backward movement therein. The locking mechanism of the closure device is preferably a tang.

The spine portion has upper and lower edges and is provided with serrations located therebetween. The tail portion has a sharpened needle end which is integral with the spine portion, to pierce intercostal tissue.

The closure device is preferably made of stainless steel, and most preferably coated with biocompatible polymer. Preferably, the spine portion of the closure device contains barbs spaced along the proximal end of the spine portion.

The present invention also embraces a method of closing the sternum in the body of a patient comprising the steps of exposing the split sternum, threading the closure device's tail portion with the integral needle end, using a needle holder, through the intercostal tissue along the outer edge of the first half of the sternum, further threading the integral needle of the closure device through the intercostal tissue along the outer edge of the second half of the sternum, inserting the tail portion into the head portion of the closure device, increasing the tension on the connected sternum by tightening the spine portion and lockingly engaging the serrations of the spine portion, cutting the excess spine portion, and locating the head in the intercostal space and closing the overlying tissue.

BRIEF DESCRIPTION OF THE DRAWINGS

Novel features and advantages of the present invention, in addition to those mentioned above, will become apparent from a reading of the following detailed description in conjunction with the accompanying drawings wherein:

FIG. 1 is a top plan view of the closure device;

FIG. 2 is a side plane view of the closure device;

DESCRIPTION OF THE PREFERRED EMBODIMENT

Figure 3:
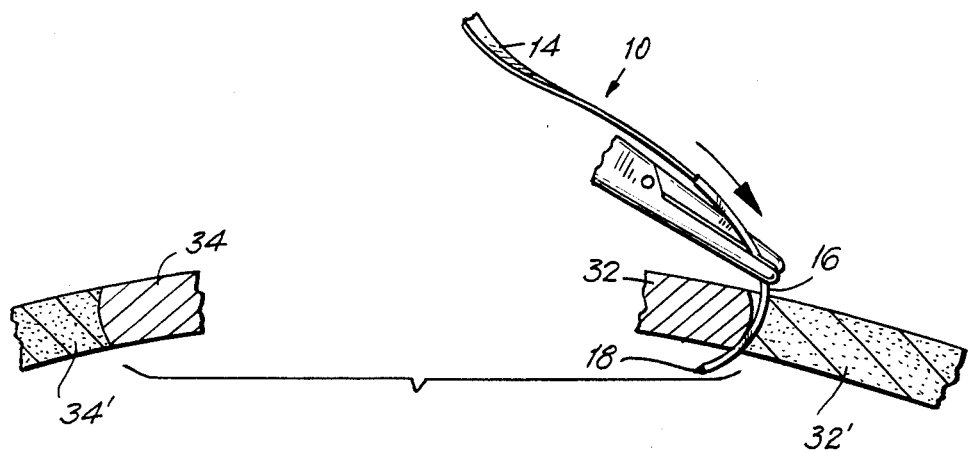
FIG. 3 is a semi-schematic view of the closure device of the present invention positioned such that the integral needle is piercing the intercostal tissue along the outer edge of the first half of the sternum.
Figure 4:
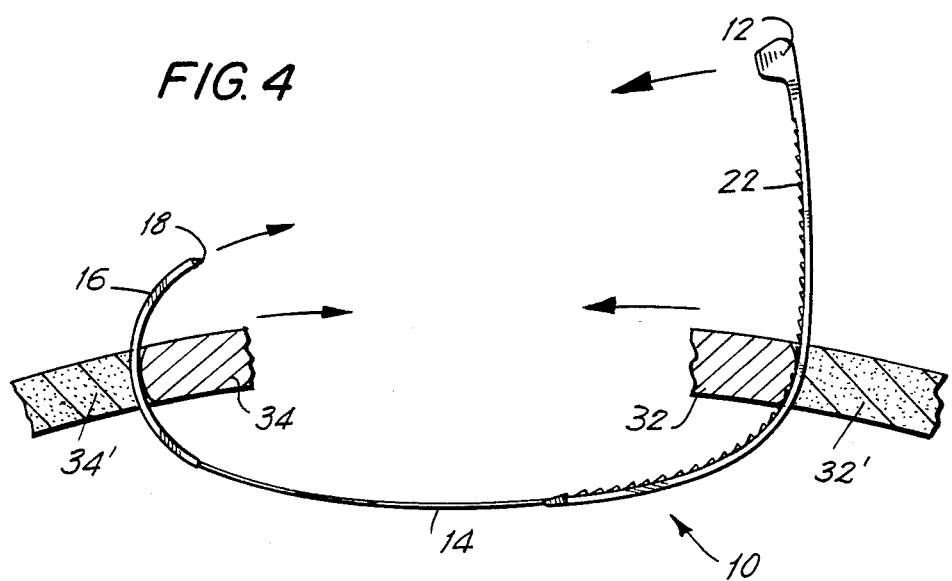
FIG. 4 is a similar view to FIG. 3 showing the tail portion with the integral needle piercing the intercostal tissue along the second half of the sternum.
Figure 5:
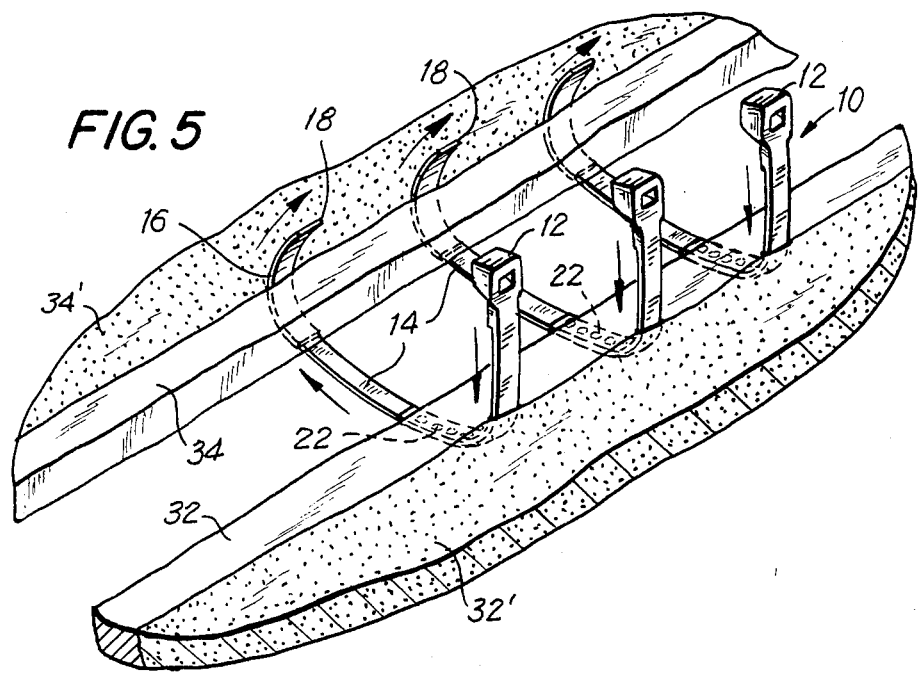
FIG. 5 is a similar view to FIG. 3 showing the closure device completely threaded around both halves of the sternum.
Figure 6:
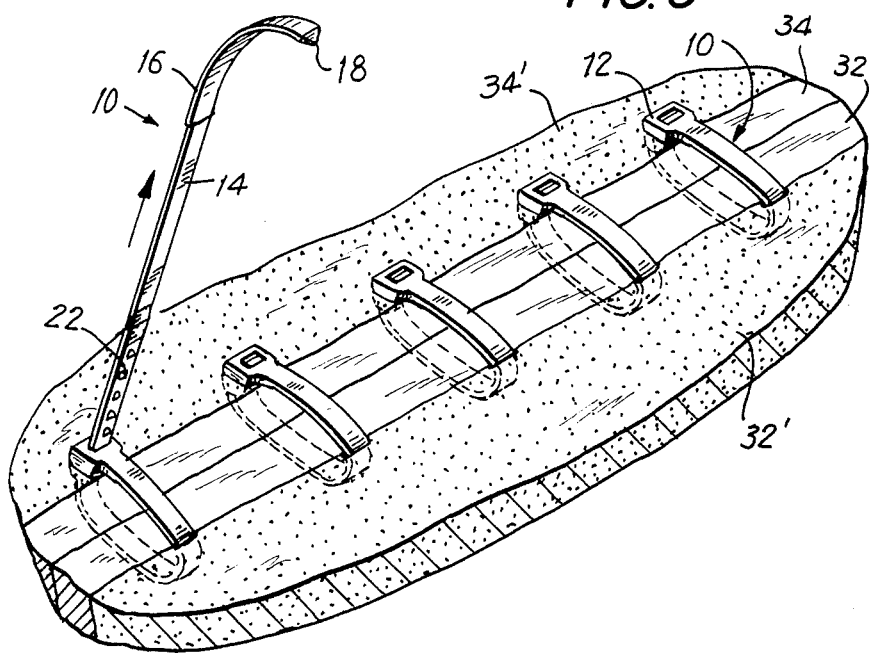
FIG. 6 is a semi-schematic view of the closure device of the invention showing the tail portion inserted into the head portion and the tightening of the spine portion having lockingly engaged the serrations of the spine portion.

In FIGS. 1–6 is illustrated a sternum closure device for closing a split sternum in the body of a patient. The sternal closure device has a smooth profile so that it may easily be inserted through the intercostal tissue and around the sternum without trauma to the tissue or bone. The sternum closure device, generally indicated at 10, includes a head portion 12, a spine portion 14 and a tail portion 16.

The head portion 12 is adapted to receive the tail portion 16 and the spine portion 14. The head portion 12 includes locking means to engage the spine portion 14 such that the spine portion 14, once engaged, is prevented from backward movement. The locking means are preferably a tang 30. The tang 30 is constructed preferably, of stainless steel shaped in the form of a tab which bites through the biocompatible polymer, thereby locking the sternum closure device 10.

The tang is preferably formed by bending or stamping the head portion 12 of the device 10. It is most preferably formed by stamping due to the resulting spring nature of the tang 30. The angle of the tang 30 relative to the spine portion 14, is preferably 20 to 45 degrees and most preferably 28 degrees, allowing ease of insertion and movement of the band through the head with maximum resistance in the reverse direction. The length of the tang 30 is preferably 0.060 to 0.080 inches, most preferably 0.067 inches. This length is proportionate to the clearance in the head portion 12. The width of the tang 30 is sized to allow total engagement of the serrations 22, preferably 0.080 wide.

The sternum closure device 10 is preferably 10 to 24 inches long, most preferably 16 to 18 inches long. The device 10 is preferably made of biocompatible metal, most preferably stainless steel, and is coated with a biocompatible polymer, preferably polyolefin, polyethylene, or polypropylene. The biocompatible polymer is applied by heat shrinking fluidize bath, or insert molding.

The spine portion 14 is preferably 0.250 inches wide by 20 inches long, most preferably 0.080 inches wide by 18 inches long. The spine portion 14 is preferably 0.005 to 0.050 inches thick, most preferably 0.010 inches thick. The serrations 22 begin preferably ⅛ to 1.5 inches proximal to the tang, most preferably 0.250 to 0.3 inches and continue preferably for 4 to 18 inches down the length of the spine, most preferably 6 inches.

The spine portion 14 further includes serrations 22 which are located between the upper and lower sides of the spine portion 14. The serrations 22 are preferably spaced 0.020 to 0.100 inches apart, most preferably 0.050 inches, and are formed by welding, cutting, or punching the steel spine. Most preferably the serrations are formed by stamping because this retains the spines original strength and flexibility.

The tail portion 16 is generally curved and begins at a point proximal to the spine portion 14 at the increased diameter of the closure device 10, and distal to the needle end 18. The tail portion 16 is formed by fastening additional material to the spine portion 14. Preferably, material is added by mechanically fastening a stiffened, folded piece of compatible material to the spine portion 14. The needle end 18 is shaped in a curved section with a round pointed tip to promote both ease of insertion and penetration of the intercostal tissue. The sharpened needle end 18 is preferably 0.005 to 0.090 inches thick, most preferably 0.030 to be able to pass through the head portion 12 without bending the tang 30. The sharpened needle end 18 is obtained by grinding, stamping or shearing.

The head portion 12 is formed by locating the spine portion 14 and tang 30 in a mold or form and preferably coating, dipping, or injection molding around it. The head is preferably a 0.1 to 0.4 inch irregular cube most preferably 0.2 inch cube so as to properly fit the human intercostal space.

In use, as shown in FIGS. 3-6, after the sternum 32, 34 has been spread, the surgeon will grasp the stiff, curved, pointed end of the device 10 and, locating the space between the ribs, push it through the intercostal tissue 32', 34' by running it along the outer edge of the sternum from the outside of the patient towards the internal cavity. It is necessary to be close to the sternum to avoid the tissue in internal cavity, to avoid the internal mammary artery which runs underneath the rib cage approximately a centimeter to either side of the sternum proper.

Having penetrated the intercostal tissue, the surgeon will grasp the end of the device from inside the body cavity and pull the device until only several inches of it is exposed. The surgeon then takes the same sharpened end of the device and introduces it from the underside of the other half of the sternum; again, staying close to the sternum bone itself.

After repeating this procedure three to five times, the surgeon will take one device at a time and connect the fastening head portion to the tail of the device.

The sternum is then approximated by squeezing on either side of the chest cavity taking care not to capture any organs or tissue. The individual devices are then pulled tight one at a time insuring that the sternum has been lined up and pressed together. It should be noted here that the head portion will be positioned just above the intercostal space so that when the device is tensioned the square closure head can be located into the space between the ribs, thereby providing a flat closure with a profile which will not be detectable once the fascia, fat and skin is closed over the incision.

The sternum closure device of the present invention eliminates many of the problems of the prior art methods of suturing the sternum. The present invention provides simple, effective means for closing a sternum in the body of a patient.

In addition, the device is of relatively uncomplicated design and offers easy manipulation with more accurate results.

Further modification will occur to those skilled in the art. The scope of the invention as defined by the appended claims and should not be understood as limited by the specific embodiments described herein.

We claim:

1. A sternum closure device comprising:
    a head portion;
    a flexible spine portion;
    and a tail portion;
    said head portion being adapted to receive said tail and spine portion, said head portion having locking means to engage said spine portion such that when the spine portion is received in the head portion the spine portion is prevented from backward movement therein;
    said spine portion being a biocompatible metal coated with a biocompatible polymer along a portion of its length, said locking means including means for piercing said biocompatible polymer to lock said closure device, said spine portion having upper and lower edges with serrations located therebetween; and
    said tail portion having a sharpened needle integral with the spine portion to pierce intercostal tissue and said head portion being adapted for location in the intercostal space.

2. The closure device of claim 1 wherein said serrations are provided by barbs spaced along the proximal end of the spine portion.

3. The closure device of claim 1 wherein the spine portion is made of stainless steel.

4. The closure device of claim 1 wherein the locking means is a tang.

5. The closure device of claim 4 wherein said tang is a first end of said spine portion, a second end being the needle bearing end.

6. The closure device of claim 5 wherein said tang is said means for piercing biocompatible polymer to lock said closure device.

7. The closure device of claim 1 wherein said biocompatible polymer is selected from the group consisting of polyethylene and polypropylene.

8. The closure device of claim 1 wherein said head portion is an irregular cubic configuration.

9. A method for closing the sternum in the body of a patient comprising the steps of:

(a) providing the device of claim 1;

(b) exposing the split sternum;

(c) threading the tail portion with the integral needle through the intercostal tissue along the outer edge of the first half of the sternum;

(d) further threading the integral needle of the closure device through the intercostal tissue along the outer edge of the second half of the sternum;

(e) inserting the tail portion into the head portion of the closure device;

(f) increasing the tension on the connected sternum by tightening the spine portion and lockingly engaging the serrations of the spine portion;

(g) cutting the excess spine portion; and (h) locating the head portion in the intercostal space and closing the overlying tissue.

* * * * *